United States Patent
Del Giudice et al.

(10) Patent No.: US 9,421,251 B2
(45) Date of Patent: Aug. 23, 2016

(54) RAPID RESPONSES TO DELAYED BOOSTER IMMUNISATIONS

(75) Inventors: Giuseppe Del Giudice, Siena (IT); Rino Rappuoli, Castelnuovo Berardenga (IT)

(73) Assignee: Novartis AG, Basel (CH)

( * ) Notice: Subject to any disclaimer, the term of this patent is extended or adjusted under 35 U.S.C. 154(b) by 386 days.

(21) Appl. No.: 12/999,848

(22) PCT Filed: Jun. 25, 2009

(86) PCT No.: PCT/IB2009/006260
§ 371 (c)(1),
(2), (4) Date: Feb. 4, 2011

(87) PCT Pub. No.: WO2009/156852
PCT Pub. Date: Dec. 30, 2009

(65) Prior Publication Data
US 2011/0150931 A1 Jun. 23, 2011

Related U.S. Application Data

(60) Provisional application No. 61/133,140, filed on Jun. 25, 2008.

(51) Int. Cl.
| | |
|---|---|
| A61K 39/085 | (2006.01) |
| A61K 39/00 | (2006.01) |
| A61K 39/08 | (2006.01) |
| A61K 39/108 | (2006.01) |
| A61K 39/09 | (2006.01) |
| A61K 39/02 | (2006.01) |
| A61K 39/145 | (2006.01) |
| A61K 39/12 | (2006.01) |

(52) U.S. Cl.
CPC ............. *A61K 39/145* (2013.01); *A61K 39/00* (2013.01); *A61K 39/12* (2013.01); *A61K 2039/545* (2013.01); *A61K 2039/55566* (2013.01); *C12N 2760/16134* (2013.01)

(58) Field of Classification Search
None
See application file for complete search history.

(56) References Cited

U.S. PATENT DOCUMENTS

| | | |
|---|---|---|
| 8,080,255 B2 | 12/2011 | Smith |
| 2007/0141078 A1 | 6/2007 | D'Hondt et al. |
| 2008/0014217 A1 | 1/2008 | Hanon et al. |

FOREIGN PATENT DOCUMENTS

| | | |
|---|---|---|
| WO | 02/080648 A | 10/2002 |
| WO | WO-2006/041978 A2 | 4/2006 |
| WO | 2006/050394 A | 5/2006 |
| WO | WO-2006/100109 A1 | 9/2006 |
| WO | WO-2006/100110 A1 | 9/2006 |
| WO | 2007/052057 A | 5/2007 |
| WO | WO-2007/052155 A2 | 5/2007 |
| WO | WO-2007/130330 A2 | 11/2007 |
| WO | WO-2008/009309 A1 | 1/2008 |
| WO | WO-2009/068992 A1 | 6/2009 |

OTHER PUBLICATIONS

Schosser et al. (IX International Jena Symposium on Tick-borne Diseases, Mar. 2007).*
Pittman et al. (Vaccine, 2002 vol. 20, pp. 2107-2115).*
La Montagne et al. (Reviews of Infectious Diseases vol. 5 No. 4, pp. 723-736).*
Stephenson, I. et al. "Boosting immunity to influenza H5N1 with MF59-adjuvanted H5N3 A/Duck/Singapore/97 vaccine in a primed human population," Vaccine, vol. 21, No. 15, 2003, pp. 1687-1693.
Mills Kingston, H.G. et al. "Protective levels of diphtheria-neutralizing antibody induced in healthy volunteers by unilateral priming-boosting intranasal immunization associated with restricted ipsilateral mucosal secretory immunoglobulin A," Infection and Immunity, vol. 71, No. 2, 2003, pp. 726-732.
Bjarnarson Stefania, P. et al. "The advantage of mucosal immunization for polysaccharide-specific memory responses in early life," European Journal of Immunology, vol. 35, No. 4, 2005, pp. 1037-1045.
Grazia, G. et al. "Fast rise of broadly cross-reactive antibodies after boosting long-lived human memory B cells primed by an MF59 adjuvanted prepandemic vaccine," Proceeding of the National Academy of Sciences of the United States of America, vol. 106, No. 19, 2003, pp. 7962-7967.
Grazia, G. et al. "Adjuvanted H5N1 vaccine induces early CD4+ T cell response that predicts long-term persistence of protective antibody levels," Proceeding of the National Academy of Sciences of the United States of America, vol. 106, No. 10, 2009, pp. 3877-3882.
Belshe et al. (2011). "Safety and immunogenicity of influenza A H5 subunit vaccines: effect of vaccine schedule and antigenic variant," J Infect Dis, 203(5):666-73.

(Continued)

*Primary Examiner* — Robert A Zeman
(74) *Attorney, Agent, or Firm* — Morrison & Foerster LLP

(57) ABSTRACT

Booster immunization can lead to rapid induction of protective immunity against pathogens (e.g. ≤7 days after the booster dose). This rapid response means that booster immunization can be used at short notice prior to an event that might require an activated immune response. For instance, a subject can be primed at a young age against a pathogen that typically affects more elderly subjects under specific circumstances such that, when the subject is older, the immune response can be mobilized rapidly if those specific circumstances are expected. An example would be to prime a subject against infections that are typically acquired nosocomially and then, soon before a scheduled hospital appointment, to boost their immune response so that they enter hospital in an immune-alert state.

5 Claims, No Drawings

(56) References Cited

OTHER PUBLICATIONS

Bender et al. (1999). "Characterization of the surface proteins of influenza A (H5N1) viruses isolated from humans in 1997-1998," Virology. 254(1):115-23.
Bresson et al. (May 20, 2006). "Safety and immunogenicity of an inactivated split-virion influenza A/Vietnam/1194/2004 (H5N1) vaccine: phase I randomised trial," *Lancet* 367(9523):1657-1664.
Carrat et al. (2007). "Influenza vaccine: The challenge of antigenic drift" Vaccine 25: 6852-6862.
Chen et al. (2005). "Avian flu: H5N1 virus outbreak in migratory waterfowl," Nature, 436:191-192.
Chun-yan et al. (Feb. 2007). "Serum-free culture of vero cells and influenza virus on microcarrier," Chin J Biologicals 20(2):125-128.
Crevar & Ross (2008) "Elicitation of protective immune responses using a bivalent H5N1 VLP vaccine," Virol J 5:131.
European Centre for Disease Prevention and Control (ECDC) Technical Report, Expert Advisory Groups on human H5N1 vaccines, Aug. 2007, 36 pages.
European Search Report mailed Jun. 14, 2013, for European Application No. 12198671, 1 page.
Forrest et al. (2009). "Single- and multiple-clade influenza A H5N1 vaccines induce cross protection in ferrets," Vaccine, 27(31):4187-95.
Fragapane et al. (2010). "A heterologous MF59-adjuvanted H5N1 prepandemic influenza booster vaccine induces a robust, cross-reactive immune response in adults and the elderly," Clin Vaccine Immunol, 17(11):1817-9.
Fukuda (2004). "Inactivated Influenza Vaccines" Chapter 17 in "Vaccines," Fourth Edition, Plotkin et al (Eds), Saunders, pp. 339-370.
Gillard et al. (2014). "Long-term booster schedules with AS03A-adjuvanted heterologous H5N1 vaccines induces rapid and broad immune responses in Asian adults," BMC Infect Dis, 14:142.
Goji et al. (2008). "Immune responses of healthy subjects to a single dose of intramuscular inactivated influenza A/Vietnam/1203/2004 (H5N1) vaccine after priming with an antigenic variant," J Infect Dis, 198(5):635-41.
Govorkova et al. (2006). "Immunization with Reverse-Genetics-Produced H5N1 Influenza Vaccine Protects Ferrets against Homologous and Heterologous Challenge," J Infect Dis. 194(2):159-167.
Haaheim (2003). "Original antigenic sin. A confounding issue?" Dev. Biologicals 115:49-53.
Hoelscher et al. (Apr. 15, 2008). "A broadly protective vaccine against globally dispersed clade 1 and clade 2 H5N1 influenza viruses," J Infect Dis 197(8):1185-1188.
Influenza Team (Sep. 20, 2007). "Human influenza A/H5N1 ("prepandemic") vaccines: informing policy development in Europe," Eurosurveillance, vol. 12, issue 38, retrieved Jan. 6, 2015 from http://www.eurosurveillance.org/ViewArticle.aspx?ArticleId=3272.
Influenza Virus Vaccine H5N1, Highlights of prescribing information, published Apr. 2007 by Sanofi Pasteur, 16 pages.
International Search Report mailed Feb. 26, 2009, for PCT Application No. PCT/IB2008/003580 filed Nov. 25, 2008, 3 pages.
Keitel et al. (Oct. 1, 2007). "Preparing for a possible pandemic: influenza A/H5N1 vaccine development," *Curr Opin Pharmacol* 7(5):484-490.
Kistner et al. (2007). "Cell culture (Vero) derived whole virus (H5N1) vaccine based on wild-type virus strain induces cross-protective immune responses," Vaccine, 25(32):6028-36.
Kistner et al. (2008). "Induction of cross-clade anti-H5N1 immune responses in mice, guinea pigs and ferrets by vero cell-derived H5N1 whole virus candidate vaccines," Poster presentations, The third European Influenza Conference, p. 34.
Leroux-Roels et al. (2007). "Antigen sparing and cross-reactive immunity with an adjuvanted rH5N1 prototype pandemic influenza vaccine: a randomised controlled trial," Lancet, 370(9587):580-9.
Li et al. (2007). "Development of vaccines against influenza A virus (H5N1).," Chang Gung Med J, 30(4):294-304.
Lipsitch et al. "Patterns of antigenic diversity and the mechanisms that maintain them," Journal of The Royal Society 4: 787-802 (2007).
NIH News (Oct. 12, 2006). "New tool helps identify mysterious viruses that caused New York respiratory illness in 2004," retrieved from the internet on Aug. 9, 2013, at <www.niaid.nih.gov/news/newsreleases/2006/Pages/masstag.aspx>.
NIH Press Release, "Updates on Pandemic Flu Vaccine Trials to be Presented at 44th Annual IDSA Meeting," NIH News, dated Oct. 12, 2006, 3 pages.
Nolan et al. (2006). "Immune responses of healthy subjects to a single dose of intramuscular inactivated influenza A/Vietnam/1203/2004 (H5N1) vaccine after priming with an antigenic variant," Late Breaker Symposium session, Infectious Diseases Society of America, 1 page.
Notice of Opposition by GlaxoSmithKline Biologicals S.A., filed in opposition against EP2211901, dated Jan. 31, 2014, 27 pages.
Oh et al. (Aug. 2010). "An antibody against a novel and conserved epitope in the hemagglutinin 1 subunit neutralized numerous H5N1 influenza viruses," J Virol 84(16):8275-86.
Poland et al. (Apr. 2007). "Avian and pandemic influenza: an overview," Vaccine 25(16):3057-61.
Preliminary non-binding opinion of the Opposition Division, filed in opposition filed in opposition against EP2211901, dated Apr. 13, 2015, 11 pages.
Rao et al. (Jun. 2008). "Multivalent HA DNA vaccination protects against highly pathogenic H5N1 avian influenza infection in chickens and mice," PLoS One 3(6):e2432.
Schwarz et al, "Single-dose primary vaccination with AS03-adjuvanted prepandemic H5N1 vaccine is sufficient to induce strong, rapid and broad immune response to booster vaccination after 12 months," GlaxoSmithKline Biologicals, filed in the opposition against EP2211901 on Sep. 23, 2014, 1 page.
Simmons et al. (May 2007). "Prophylactic and therapeutic efficacy of human monoclonal antibodies against H5N1 influenza," PLoS Med 4(5):e178.
Smith et al. (2006). "Evolution and adaptation of H5N1 influenza virus in avian and human hosts in Indonesia and Vietnam" Virology 350: 258-268.
Stephenson et al. (2004). "Confronting the avian influenza threat: vaccine development for a potential pandemic," Lancet Infect Dis. 4(8):499-509.
Stephenson (2005). "Are we ready for pandemic influenza H5N1?" Expert Rev Vaccines, 4(2):151-5.
Stephenson et al. (May 2006). "Phase I Evaluation of Intranasal Trivalent Inactivated Influenza Vaccine with Nontoxigenic *Escherichia coli* Enterotoxin and Novel Biovector as Mucosal Adjuvants, Using Adult Volunteers," *J Virol* 80(10):4962-4970.
Stephenson et al. (Oct. 9, 2008). "Antigenically distinct MF59-adjuvanted vaccine to boost immunity to H5N1," *NEJM* 359(15):1631-1633.
Treanor et al. (2001). "Safety and immunogenicity of a recombinant hemagglutinin vaccine for H5 influenza in humans," Vaccine, 19(13-14):1732-7.
Treanor et al. (2006). "Safety and immunogenicity of an inactivated subvirion influenza A (H5N1) vaccine," N Engl J Med, 354(13):1343-51.
van der Velden et al. (2012). "Cell culture (Vero cell) derived whole-virus non-adjuvanted H5N1 influenza vaccine induces long-lasting cross-reactive memory immune response: homologous or heterologous booster response following two dose or single dose priming," Vaccine, 30(43):6127-35.
WHO (2010-2015). Recommended viruses for influenza vaccines for use in the 2010-2011, 2011-2012, 2013-2014, 2014-2014 northern hemisphere influenza season.
WHO (Oct. 2011). "Updated unified nomenclature system for the highly pathogenic H5N1 avian influenza viruses," Retrieved Jan. 29, 2014 from <http://www.who.int/influenza/gisrs_laboratory/h5n1_nomenclature/en/>.
WHO/OIE/FAO H5N1 Evolution Working Group. (2008). "Toward a unified nomenclature system for highly pathogenic avian influenza virus (H5N1)," Emerg Infect Dis, 14(7):e1.
Yang et al. (2012). "Multiple-clade H5N1 influenza split vaccine elicits broad cross protection against lethal influenza virus challenge in mice by intranasal vaccination," PLoS One, 7(1):e30252.

(56) References Cited

OTHER PUBLICATIONS

Response to the final Office Action, filed in U.S. Appl. No. 12/744,920 on Jul. 9, 2015. 11 pages.

Response to Notice of Opposition by patentee, filed in opposition against EP2211901, dated Sep. 23, 2014, 16 pages.

Response to oral proceedings' summons by GlaxoSmithKline, filed in opposition filed in opposition against EP2211901, dated Aug. 26, 2015, 10 pages.

Response to oral proceedings' summons by Novartis, filed in opposition filed in opposition against EP2211901, dated Aug. 27, 2015, 5 pages.

Response to oral proceedings' summons by GlaxoSmithKline, filed in opposition filed in opposition against EP2211901, dated Sep. 16, 2015, 3 pages.

Response with regard to oral proceedings by GlaxoSmithKline, filed in opposition filed in opposition against EP2211901, dated Oct. 22, 2015, 2 pages.

* cited by examiner

RAPID RESPONSES TO DELAYED BOOSTER IMMUNISATIONS

This application is the U.S. National Phase of International Patent Application No. PCT/IB2009/006260, filed 25 Jun. 2009 and published in English, which claims the benefit of U.S. provisional patent application 61/133,140, filed 25 Jun. 2008, the complete contents of which are incorporated herein by reference.

TECHNICAL FIELD

This invention is in the field of immunization.

BACKGROUND ART

The use of a prime-boost immunization schedule is well known. For example, children typically receive a variety of primary immunizations up to the age of 15 months (e.g. a DTPa vaccine) and then receive booster doses aged between 4-6 years and beyond (e.g. a Tdap vaccine). According to current schedules, though, the immune response elicited by a booster dose does not lead to rapid re-establishment of immunity (e.g. of protective antibody titers). Furthermore, the primary immunizations aim to provide immediate protection against diseases that affect the pediatric population, and the aim of a booster is to prolong this immediate protection.

DISCLOSURE OF THE INVENTION

It has now been found that booster immunization can lead to rapid induction of protective immunity against pathogens (e.g. ≤7 days after the booster dose), even if priming doses had been given several years before and had not established protective immunity. This rapid response to delayed boosting means that booster immunization can be used at short notice prior to an event that might require an activated immune response, and the priming dose is used to prepare the immune system for providing rapid protection when is needed later. Thus the aim of a boosting dose can be to conclude protection rather than prolong it. The rapid response means that booster immunization can be used at short notice prior to an event that might require an activated immune response. For instance, a subject can be primed at a young age against a pathogen that typically affects more elderly subjects under specific circumstances such that, when the subject is older, the immune response can be mobilized rapidly if those specific circumstances are expected. An example would be to prime a subject against infections that are typically acquired nosocomially (e.g. MRSA, *Clostridium difficile*) and then, soon before a scheduled hospital appointment, to boost their immune response so that they enter hospital in an immune-alert state. Another example would be to prime a female during adolescence against infections that are typically passed on during childbirth (e.g. group B *streptococcus, S. agalactiae*) and then, before birth, boost their immune response so that they have useful anti-GBS immunity at the time of delivery.

It has also been found that this prime/boost approach can be effective even if the pathogen has antigenically drifted since the priming immunization. Thus the priming immunization can be 'future proof', allowing it to be administered many years before the risk of infection.

Thus the invention provides a method for raising an immune response in a subject, comprising steps of: (i) administering at least one dose of a priming immunogenic composition to the subject, wherein the priming immunogenic composition elicits a primary immune response against a pathogen; and then (ii) administering a boosting immunogenic composition to the subject, wherein the boosting immunogenic composition elicits, within 21 days (or sooner) of its administration, a protective anamnestic immune response against the pathogen.

The invention also provides a method for priming a subject, comprising a step of administering a priming immunogenic composition to the subject, wherein the priming immunogenic composition elicits a primary immune response against a pathogen allowing the establishment of immunological memory, wherein the subject will later receive a boosting immunogenic composition that will, within 21 days of its administration (or sooner), elicit a protective anamnestic immune response against the pathogen.

The invention also provides a method for eliciting in a subject a protective anamnestic immune response against a pathogen, comprising a step of administering a boosting immunogenic composition to the subject, wherein: (i) the boosting immunogenic composition elicits, within 21 days of its administration (or sooner), a protective anamestic immune response against the pathogen; and (ii) the subject previously received a priming immunogenic composition that elicited a primary immune response against the pathogen.

As explained below, inclusion of an adjuvant in a boosting composition is preferred.

The Pathogen

The invention can be used to immunize against a variety of pathogens. It is ideally suited for immunizing against diseases that, in general, occur in adult life rather than in childhood. Similarly, it is well suited for immunizing against pathogens that are not covered by current childhood immunization schedules (*C. diphtheriae, C. tetani, B. pertussis*, poliovirus, hepatitis B virus, *H. influenzae* type B, *N. meningitidis, S. pneumoniae*, measles virus, mumps virus, rubella virus, rotavirus, H3N2 and H1N1 influenza A viruses, influenza B virus, varicella zoster virus, hepatitis A virus, human papillomavirus). The invention is very useful against pathogens that, in general, are transmitted nosocomially. The invention is also useful against pathogens that, in general, are transmitted during birth. In some embodiments of the invention the pathogen is not an influenza A virus having a H5 hemagglutinin.

Thus the invention can be used to immunize against pathogens such as, but not limited to: *Staphylococcus aureus* (including MRSA strains), *Clostridium difficile*, Coagulase-negative *Staphylococcus* species ('CoNS', including *S. haemolyticus* and *S. epidermidis*), *Candida* strains (such as *C. albicans*), Enterococci, *Klebsiella pneumoniae*, Acinetobacter species, *Pseudomonas aeruginosa, Streptococcus agalactiae, Streptococcus pyogenes*, and extraintestinal pathogenic *Escherichia coli* ('ExPEC'). Immunogens from these pathogens are known e.g. references 1 to 18.

The pathogen may exist in multiple different pathogenic variants. Depending on the particular pathogen then such variants may be e.g. serogroups, serotypes, immunotypes, serovars, biovars, strains, clades, or species.

The Human Subject

A subject receives at least one dose of priming composition and at least one dose of boosting composition. In some embodiments the criteria for administering the priming composition are wide, but the criteria for administering the boosting composition are narrower e.g. the priming composition might be given to substantially all children in a given population, whereas the boosting composition is given only to adults at specific risk of infection by from the relevant pathogen. In other embodiments the priming and boosting compositions are administered at substantially the same breadth as each other.

The subject (particularly at the time of the boosting dose) may be at increased risk (e.g. higher risk than the general population) of hospitalization, and thus of catching a nosocomial infection. Such subjects include, but are not limited to: subjects with increased risk of burns, such as firefighters or members of armed forces; subjects with increased risk of wounds, such as members of armed forces or police services; healthcare workers, such as physicians, surgeons or nurses; veterinarians; nursing home inhabitants; patients preparing for or undergoing invasive medical procedures; subjects preparing for cosmetic surgery; subjects preparing for, receiving or with prosthetic implants e.g. heart valves, joints, chronic vascular catheters, cosmetic implants; hemodialysis patients e.g. with end-stage renal disease; patients with continuous ambulatory peritoneal dialysis; diabetic patients; patients aged at least 65 e.g. $\geq 70$, $\geq 75$, $\geq 80$, $\geq 85$, $\geq 90$; patients with dermatologic conditions; users of illicit intravenous drugs; HIV positive patients; cancer patients; coronary artery bypass patients; and transplant patients.

The subject may be female, particularly where the pathogen is *S. agalactiae*.

Priming and Boosting Doses

A subject receives at least one dose of priming composition and at least one dose of boosting composition. The priming and boosting compositions will typically be administered more than 1 year apart, e.g. $\geq 14$ months apart, $\geq 16$ months apart, $\geq 18$ months apart, $\geq 2$ years apart, $\geq 5$ years apart, $\geq 10$ years apart, $\geq 15$ years apart, $\geq 20$ years apart, $\geq 25$ years apart, $\geq 30$ years apart, $\geq 35$ years apart, $\geq 40$ years apart, $\geq 45$ years apart, $\geq 50$ years apart, etc.

The priming composition elicits a primary immune response against a pathogen. Thus it will typically elicit both an antibody response and memory B cells against the pathogen. Its effect is to prepare the immune system for later exposure to the boosting composition. More than one dose of priming composition may be given e.g. two doses. In some embodiments the priming composition protects (at least temporarily) the subject against infection and/or disease caused by the pathogen. In other embodiments the priming composition does not protect the subject against infection and/or disease caused by the pathogen, and such protection will be provided by the boosting composition.

The priming composition(s) may be administered with one or more other vaccine(s). For example, a priming composition may be administered to a subject at substantially the same time as (e.g. during the same medical consultation or visit to a healthcare professional or vaccination centre) a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a pneumococcal conjugate vaccine, a rotavirus vaccine, an influenza virus vaccine, a hepatitis A virus vaccine, a herpes simplex virus vaccine, and/or a human papillomavirus virus (HPV) vaccine. For instance, a priming immunization against *S. agalactiae* may be given between 11-18 years e.g. at the same time as a Tdap vaccine, a HPV vaccine, a meningococcal conjugate vaccine, etc.

Because of administration of the previous priming composition, the boosting composition elicits a secondary immune response against the pathogen. Thus the memory B cells that were elicited by the priming composition are activated, and they can rapidly proliferate and differentiate into plasma cells that secrete high-affinity serum antibodies. The result is that the subject mounts an anamnestic immune response that is protective against infection and/or disease caused by the pathogen.

The protective anamnestic immune response will generally comprise at least an antibody response, and the antibody response may include neutralizing and/or opsonizing antibodies.

The anamnestic immune response is mounted by the subject within 21 days of receiving the boosting composition e.g. $\leq 20$ days, $\leq 19$ days, $\leq 18$ days, $\leq 17$ days, $\leq 16$ days, $\leq 15$ days, $\leq 14$ days, $\leq 13$ days, $\leq 12$ days, $\leq 11$ days, $\leq 10$ days, $\leq 9$ days, $\leq 8$ days, $\leq 7$ days, $\leq 6$ days, $\leq 5$ days, $\leq 4$ days, $\leq 3$ days, $\leq 2$ days, or even $\leq 1$ day. In preferred embodiments the subject mounts a protective anamnestic immune response within $\leq 7$ days of receiving the boosting composition.

In some embodiments the boosting composition is administered prior to a specific event e.g. before a hospital appointment, before a trip abroad, before a tour of duty, before battle, before giving birth, before entering a nursing home as an inhabitant, before an invasive medical procedure or operation, before receiving a prosthetic implant, before hemodialysis, before receiving chemotherapy, before receiving radiotherapy, etc. In such embodiments the boosting composition is administered at least as far prior to the event as the duration required for the protective anamnestic immune response e.g. if it takes 7 days to achieve a protective anamnestic immune response then the boosting composition will be administered at least 7 days in advance of the event. Typically, however, the boosting composition will not be administered too far in advance e.g. no more than a year prior to the event.

In other embodiments the boosting composition is administered when planning for a specific event. For instance, if pregnancy is planned then the boosting composition can be administered to a female before conception, or after conception, to provide the protective anamnestic immune response ready for birth.

In other embodiments the boosting composition is administered at an arbitrary time unrelated to a particular event e.g. at a particular age.

The priming composition and boosting composition each contain an immunogen that elicits an immune response against the same pathogen. The priming immunogen and boosting immunogen will each typically comprise a T-dependent antigen. They may include the same immunogen or different immunogens. The immunogen can take any suitable form e.g. it may comprise a protein, a conjugated saccharide, outer membrane vesicles, inactivated whole cells, etc.

If the pathogen exists in multiple different pathogenic variants then the priming immunogen and the boosting immunogen may be from the same variant or from different variants. For example, the priming and boosting immunogen may be from different serogroups, different serotypes, different immunotypes, different serovars, different biovars, different strains, different clades, or different species of the same pathogen. With H5 influenza, for instance, a boosting hemagglutinin may be from a different clade from a priming hemagglutinin.

The priming composition and/or the boosting composition may include an immunological adjuvant.

The priming composition and/or the boosting composition may be administered by the same route or by different routes. Suitable routes include, but are not limited to, intramuscular injection (e.g. into the arm or leg), subcutaneous injection, intranasal, oral, intradermal, transcutaneous and transdermal.

Natural Priming

As an alternative to administering a priming dose, a natural infection may serve to prime a subject's immune response. The infection may be with the same pathogen or an immunologically related pathogen (e.g. as in the cowpox/smallpox immunological relationship). Where the infection is with the same pathogen species, but the pathogen exists in multiple different pathogenic variants, the booster dose may be such a variant e.g. from a different serogroup, serotype, immunotype, serovar, biovar, strain, or clade of the species which previously caused the natural infection.

The boosting composition will typically be administered more than 1 year after the natural infection, e.g. ≥14 months later, ≥16 months later, ≥18 months later, ≥2 years later, ≥5 years later, ≥10 years later, ≥15 years later, ≥20 years later, ≥25 years later, ≥30 years later, ≥35 years later, ≥40 years later, ≥45 years later, ≥50 years later, etc.

Because of the previous infection, the boosting composition elicits a secondary immune response against the pathogen. Thus the memory B cells that were elicited by the infection are activated, and they can rapidly proliferate and differentiate into plasma cells as described above.

Thus the invention provides a method for eliciting in a subject a protective anamnestic immune response against a pathogen, comprising a step of administering a boosting immunogenic composition to the subject, wherein: (i) the boosting immunogenic composition elicits, within 21 days of its administration (or sooner), a protective anamnestic immune response against the pathogen; and (ii) previous infection had caused the subject to mount a primary immune response against the pathogen.

Medical Uses

The invention also provides an immunogen for use in a method of the invention.

The invention also provides the use of an immunogen in the manufacture of a vaccine for protecting a subject against disease and/or infection caused by a pathogen, wherein (i) the subject previously received a priming immunogenic composition that elicited a primary immune response against the pathogen, and (ii) the vaccine elicits, within 21 days of its administration, a protective anamnestic immune response against the pathogen.

The invention also provides the use of an immunogen in the manufacture of a vaccine for priming a subject's immune system for later boosting, wherein the boosting elicits, within 21 days of its administration, a protective anamnestic immune response against a pathogen, and the priming elicits a primary immune response against the pathogen.

The invention also provides an immunogen for use in a method for raising a primary immune response against a pathogen in a subject comprising a step of administering a priming immunogenic composition to the subject, wherein the subject will later receive a boosting immunogenic composition that will, within 21 days of its administration, elicit a protective anamnestic immune response against the pathogen.

The invention also provides an immunogen for use in a method for raising a booster immune response against a pathogen in a subject comprising a step of administering a boosting immunogenic composition to the subject, wherein: (i) the boosting immunogenic composition elicits, within 21 days of its administration, a protective anamnestic immune response against the pathogen; and (ii) the subject previously received a priming immunogenic composition that elicited a primary immune response against the pathogen.

The invention also provides the use of an immunogen in the manufacture of a vaccine for protecting a subject against disease and/or infection caused by a pathogen, wherein (i) previous infection of the subject had caused it to mount a primary immune response against the pathogen, and (ii) the vaccine elicits, within 21 days of its administration, a protective anamnestic immune response against the pathogen.

The invention also provides an immunogen for use in a method for raising a booster immune response against a pathogen in a subject comprising a step of administering a boosting immunogenic composition to the subject, wherein: (i) the boosting immunogenic composition elicits, within 21 days of its administration, a protective anamnestic immune response against the pathogen; and (ii) previous infection had caused the subject to mount a primary immune response against the pathogen.

Adjuvant(s)

The priming composition and/or the boosting composition may include an immunological adjuvant to enhance the immune responses (humoral and/or cellular) elicited in a subject. If both of the compositions include an adjuvant, they may include the same adjuvant or different adjuvants. If only one of the two vaccines is adjuvanted then preferably it is the second. The use of an adjuvanted booster dose is shown below (study I) to be effective, and the use of adjuvanted priming and boosting doses gave the best protective anamnestic immune responses.

Suitable adjuvants for use with the invention include, but are not limited to, mineral-containing compositions and oil-in-water emulsions.

Mineral-containing compositions can include calcium salts, aluminum salts, or mixtures thereof. Suitable calcium salts include calcium phosphate (e.g. the "CAP" particles disclosed in ref. 19). Suitable aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [20].

The adjuvants known as aluminum hydroxide and aluminum phosphate may be used. These names are conventional, but are used for convenience only, as neither is a precise description of the actual chemical compound which is present (e.g. see chapter 9 of reference 24). The invention can use any of the "hydroxide" or "phosphate" adjuvants that are in general use as adjuvants.

The concentration of $Al^{+++}$ in a composition for administration to a subject is preferably less than 10 mg/ml e.g. ≤5 mg/ml, ≤4 mg/ml, ≤3 mg/ml, ≤2 mg/ml, ≤1 mg/ml, etc. A useful range is between 0.3 and 1 mg/ml. A maximum of 0.85 mg/dose is preferred.

Oil-in-water emulsions have been found to be particularly suitable for adjuvanting vaccines. Various such emulsions are known, and they typically include at least one oil (e.g. squalene) and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [21-23], as described in more detail in Chapter 10 of ref. 24 and chapter 12 of ref. 25. The MF59 emulsion advantageously includes citrate ions e.g. 10 mM sodium citrate buffer.

An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. An adjuvant containing (per 0.25 ml or per dose) 10.68 mg squalene, 11.86 mg DL-α-tocopherol and 4.86 mg polysorbate 80 is ideal.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [26]. The emulsion may also include one or more of alditol; a cryoprotective agent (e.g. a sugar, such as dodecylmaltoside and/or sucrose); and/or an alkylpolyglycoside. Such emulsions may be lyophilized.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

MODES FOR CARRYING OUT THE INVENTION

Human Study I [27,28]

Subjects were primed with an influenza vaccine prepared from H5N3 strain A/duck/Singapore/1997 (clade 0). The vaccine was either unadjuvanted (group 2) or was adjuvanted with the MF59 squalene-in-water emulsion (group 1). A third group of subjects (group 3) did not receive the H5N3 vaccine.

After 6 to 8 years, and at a time of heightened risk of a pandemic H5N1 outbreak, subjects were immunized with an influenza vaccine prepared from a H5N1 strain (clade 1 or 2). Two doses were administered, at days 0 & 21, both with MF59 adjuvant. Thus groups 1 and 2 received a boosting composition.

Results are shown in Table I.

Geometric mean antibody titers and sero-responses were significantly higher in primed subjects than in unprimed subjects. By day 7 after one dose of vaccine, ≥80% of MF59-H5 primed recipients achieved seroprotective HAI titers of ≥1:40 to all clade 1, 2.1, 2.2, and 2.3 avian H5 virus variants tested as well as the original A/duck/Singapore/1997 clade 0 antigen.

Subjects who had previously been primed by the clade 0 vaccine mounted a better and more rapid immune response against the new clade than the un-primed subjects. Among primed subjects, protective cross-reacting antibody titers to diverse H5N1 virus variants were seen by day 7 after a single boosting dose. Within the primed group, subjects who had received an adjuvanted priming dose mounted a better immune response than subjects who had received an unadjuvanted prime.

Although these results were obtained using influenza virus, they offer proof of principle that a priming dose of a vaccine can be administered to subjects at a time of low risk of infection by the relevant pathogen, and then their immune system can be boosted several years later at a time of heightened risk to provide protective levels of immunity in less than a week. This finding is applicable not only to H5 influenza but to a wide range of pathogens, particularly those that are often caught in hospitals.

Human Study II [30]

A phase II clinical study was performed to evaluate the immunogenicity in adults aged 19-61 of one or two booster administrations of a monovalent AS03-adjuvanted vaccine containing 3.75 μg HA from H5N1 A/Indonesia/5/05. The patients had previously (about 14-months earlier) been vaccinated with two doses of a pandemic candidate vaccine containing 3.8, 7.5, 15 or 30 μg HA from H5N1 A/Vietnam/1194/2004, with or without AS03 adjuvant (i.e. 8 groups in total). This study mimics an outbreak which occurs after priming subjects with a pandemic vaccine based on a H5N1 strain heterologous to the emerging pandemic strain.

Analysis of the priming study showed that two administrations of non-adjuvanted vaccine was not sufficient to elicit an immune response considered as protective according to currently used regulatory criteria (from the CHMP and CBER). These subjects (4 groups) received two administrations of the A/Indonesia/5/05 vaccine; other subjects received a single booster vaccine; a control group of unprimed subjects received two doses of the A/Indonesia/5/05 vaccine.

A proportion of subjects who had been immunized 14 months previously (whether the priming vaccines were adjuvanted or unadjuvanted) became seropositive 7 days after receiving one dose of the booster vaccine, compared to the control subjects. Seropositivity rates were higher in subjects who had received adjuvanted priming vaccine. 21 days after the last booster vaccination, a majority of subjects in all groups became seropositive.

The ≥40% seroconversion rate threshold required by the European Committee for Medicinal Products for Human Use (CHMP) for adults aged 18-60 years was exceeded 7 days after boosting in subjects who had received adjuvanted priming vaccine, and the seroconversion rate remained high 21 days after vaccination. In subjects whose priming vaccines had been unadjuvanted, the ≥40% seroconversion rate was also exceeded 7 days after the first vaccination, although the lower limit of the 95% confidence interval for seroconversion was inferior to the threshold for the 7.5 and 15 μg group.

When primed with an adjuvanted vaccine from a strain different from the boosting strain, subjects develop adequate seroprotective humoral responses directed against the boosting strain. The capacity to rapidly (as soon as within 7 days) develop a seroprotective response against a strain drifted from the strain used in the primary vaccination is sustained as long as 14 months, when subjects have been primed with an adjuvanted vaccine and are boosted with adjuvanted vaccine. HI antibodies levels obtained after boosting with an adjuvanted vaccine at either 6 or 14 months after primary vaccination with an adjuvanted vaccine are similar, when using a vaccine strain drifted from the primary strain for boosting and when testing against the strain used for boosting.

Persistent cross-clade CD4-positive and memory B cell responses were detected 14 months after primary vaccination with adjuvanted vaccine. These responses were higher as compared to subjects whose priming dose was unadjuvanted. Increases in cross-clade CD4-positive and memory B cell responses were observed in all groups, but were higher in subjects whose priming vaccines were adjuvanted.

Human Study III [29]

Healthy volunteers aged 18 to 59 years receive a single priming vaccination of a whole virion Vero cell-derived H5N1 (A/Vietnam/1203/2004) influenza vaccine at day zero, and a single boosting dose (A/Indonesia/05/2005) is given a year later.

The primary measure of the study is the number of subjects with an antibody response to the vaccine strain associated with protection 21 days after the booster vaccination, defined as the titer measured by microneutralization test >=1:20. The secondary measure is the number of subjects with an antibody response associated with protection 21, 42, 180 and 360 days after the priming vaccination and 21 days after the booster vaccination.

Human Study IV [30]

Healthy adults aged 18-60 years received two doses of monovalent adjuvanted egg-derived split H5N1 vaccine, spaced by either 6 months or 12 months. The adjuvant was "AS03", an oil-in-water emulsion comprising squalene. Antigen dose was 3/75 µg HA per dose. Two different vaccines were used; "VT", containing antigen from the A/VietNam/1194/2005 strain (clade 1); and "IN", containing antigen from the A/Indonesia/5/2005 strain (clade 2.1). Four groups of patients (about 65 patients per group) were immunized as follows:

| Group | First vaccine | Time of second vaccine | Second vaccine |
|---|---|---|---|
| A | VT | 6 months | VT |
| B | VT | 12 months | VT |
| C | VT | 6 months | IN |
| D | VT | 12 months | IN |

Seropositivity rates and GMTs were measured at time zero, 3 weeks later, at the time of the second vaccine, one week after the second vaccine, and three weeks after the second vaccine. Data from groups B and D are not yet available; data from groups A and C were as follows:

| | A | | C | |
|---|---|---|---|---|
| | SP % | GMT | SP % | GMT |
| Antibodies against A/Indonesia/5/2005 | | | | |
| Zero | 0% | 5.0 | 0% | 5.0 |
| +3 weeks | 12.7% | 5.6 | 14.3% | 6.3 |
| Second dose | 4.1% | 5.3 | 7.3% | 5.5 |
| +1 week | 78.7% | 64.6 | 98.1% | 152.9 |
| +3 weeks | 85.4% | 92.4 | 98.1% | 303.4 |
| Antibodies against A/Vietnam/1194/2005 | | | | |
| Zero | 3.6% | 5.3 | 0% | 5.0 |
| +3 weeks | 50.9% | 16.3 | 55.4% | 20.9 |
| Second dose | 36.7% | 9.7 | 45.5% | 12.0 |
| +1 week | 89.4% | 202.6 | 98.1% | 226.3 |
| +3 weeks | 89.6% | 287.2 | 98.1% | 434.7 |

All groups who received a booster dose after 6 months mounted a rapid and effective immune response, showing a significant increase in GMTs for HI antibodies against the A/Indonesia/5/2005 and the A/Vietnam/1194/2004 strains at both post-booster time points. Moreover, within 7 days of the booster dose, all groups met the CHMP seroconversion threshold (≥40% seroconversion, using day 0 as a baseline) for both strains, and the response was sustained until at least 14 days later.

The vaccine was shown to confer broad cross-clade immunity which was maintained even when (i) the second dose was given many months after the first dose, and (ii) the second dose was from a different H5N1 strain. In comparison with further data, two vaccination doses, whether given 21 days or six months apart, were shown to elicit a comparable immune response against the vaccine strain, confirming that the timing of administration of the second dose can be flexible and undertaken up to six months after first immunization while maintaining the quality of the immune response.

A one-dose priming administration followed 6 months later by a booster dose containing a heterologous vaccine strain meets or exceeds all relevant CHMP and FDA criteria for these vaccines. Professor Albert Osterhaus, Head Department of Virology, Institute of Virology Erasmus Medical Centre Rotterdam, confirmed that the vaccine used in this study "provides broad and persistent immunity, also against drifted H5N1 strains" and that "this level of immunity can be maintained when the second dose is given many months after the first, even with a different H5N1 strain."

Human Study V

Subjects received an adjuvanted whole virion Vero-derived H5N1 (A/Vietnam/1203/2004) influenza vaccine for immunological priming. Six different formulations were used for priming (4 adjuvanted HA doses of 3.75 µg, 15 µg or 30 µs per dose; 2 unadjuvanted HA doses of 7.5 µg or 15 µg). 12-17 months later, 77 patients received a boosting dose containing 7.5 µg HA from a different H5N1 strain (A/Indonesia/05/2005) Immune responses were assessed using a microneutralisation test against wild-type A/Indonesia/05/2005, using sera collected at days 0 (priming), 21, 42 and 180, and then at days 0 (booster dose), 7 and 21. GMT values were in the range 0-20 in all groups after priming, up to receipt of the booster dose. The boosting dose then caused GMTs to rise sharply: 7 days later GMT values were in the range of 50-100, and within 21 days of the booster dose GMTs were in the range 80-220. The percentage of subjects with neutralizing antibody responses (MN titer ≥20) in the booster phase were as follows:

| HA dose: | 3.75 µg | 7.5 µg | 7.5 µg | 15 µg | 15 µg | 30 µg |
|---|---|---|---|---|---|---|
| Adjuvant: | + | + | − | + | − | + |
| MN against A/Indonesia/05/2005 | | | | | | |
| Day 0 | 0 | 7 | 0 | 0 | 0 | 8 |
| Day 7 | 81 | 93 | 91 | 92 | 100 | 100 |
| Day 21 | 94 | 100 | 100 | 100 | 88 | 100 |
| MN against A/Vietnam/1203/2004 | | | | | | |
| Day 0 | 12 | 13 | 25 | 15 | 50 | 25 |
| Day 7 | 81 | 93 | 91 | 92 | 100 | 92 |
| Day 21 | 94 | 93 | 92 | 100 | 100 | 100 |

Overall, the results show that the vaccine induces memory B cells which can provide an immediate antibody response to later H5N1 infection. A single heterologous boost 12-17 months after the primary immunization resulted in the rapid induction of very high titers against both the initial vaccine and the booster strain, providing 90-100% seroprotection 7 days after the booster vaccination. Moreover, the rapid induction of a protective immune response was achieved not only against the clade 1 priming strain and the clade 2 boosting strain, but also against representative viruses of clade 2.2 (turkey/Turkey) and 2.3 (Anhui).

It will be understood that the invention has been described by way of example only and modifications may be made whilst remaining within the scope and spirit of the invention.

TABLE I

| Measure | G1 | G2 | G3 |
|---|---|---|---|
| % of subjects with HI titer ≥40 | | | |
| at day 0 | 0 | 0 | 3 |
| at day 8 | 75 | 56 | 12 |
| at day 15 | 90 | 60 | 9 |
| at day 22 | 75 | 58 | 13 |
| at day 43 | 75 | 58 | 45 |
| % of subjects with seroconversion | | | |
| at day 8 | 75 | 56 | 8 |
| at day 15 | 90 | 60 | 10 |
| at day 22 | 75 | 58 | 14 |
| at day 43 | 75 | 58 | 45 |
| Geometric mean HI at | | | |
| day 1 | 4 | 4 | 4.9 |
| day 8 | 72 | 51 | 5.9 |
| day 15 | 256 | 79 | 7.3 |
| day 22 | 112 | 52 | 8.0 |
| day 43 | 95 | 44 | 26 |
| Ratio of HI relative to day 1 | | | |
| at day 8 | 18 | 13 | 1.3 |
| at day 15 | 64 | 20 | 1.56 |
| at day 22 | 28 | 13 | 1.8 |
| at day 43 | 24 | 11 | 5.9 |
| % of subjects with MN titer ≥80 | | | |
| at day 0 | 0 | 0 | 0 |
| at day 8 | 9 | 5 | 1 |
| at day 15 | 9 | 9 | 1 |
| at day 22 | 12 | 9 | 1 |
| at day 43 | 12 | 10 | 5 |
| Geometric mean MN titer at | | | |
| day 1 | 10 | 10 | 10 |
| day 8 | 219 | 151 | 11 |
| day 15 | 1145 | 473 | 12 |
| day 22 | 375 | 324 | 12 |
| day 43 | 415 | 241 | 33 |
| Ratio of MN relative to day 1 | | | |
| at day 8 | 22 | 15 | 1.1 |

TABLE I-continued

| Measure | G1 | G2 | G3 |
|---|---|---|---|
| at day 15 | 115 | 47 | 1.2 |
| at day 22 | 37 | 32 | 1.2 |
| at day 43 | 41 | 24 | 3.3 |

REFERENCES

[1] Shinefield (2006) *Vaccine* 24 Suppl 2:S2-65-9.
[2] Halsey (2008) *Am J Health Syst Pharm.* 65(8):705-15.
[3] Wang & Barrett (2007) *Methods Mol Biol* 391:209-25.
[4] Maira-Litran et al. (2004) *Vaccine.* 22(7):872-9.
[5] WO2007/113222.
[6] WO2006/032500.
[7] WO2003/097091.
[8] Koch et al. (2004) *Vaccine* 22(7):822-30.
[9] Egorova et al. (1997) *Zh Mikrobiol Epidemiol Immunobiol.* (6):96-101.
[10] Szostak et al. (1994) *J Biotechnol.* 44(1-3):161-70.
[11] Solov'ev et al. (2006) *Zh Mikrobiol Epidemiol Immunobiol.* (1):20-5
[12] Kurupati et al. (2006) *Proteomics* 6(3):836-44.
[13] U.S. Pat. No. 5,955,090.
[14] Döring & Pier (2008) *Vaccine* 26(8):1011-24.
[15] WO02/34771.
[16] WO2006/089264.
[17] WO2006/091517.
[18] WO2008/020330.
[19] U.S. Pat. No. 6,355,271.
[20] WO00/23105.
[21] WO90/14837.
[22] Podda & Del Giudice (2003) *Expert Rev Vaccines* 2:197-203.
[23] Podda (2001) *Vaccine* 19: 2673-2680.
[24] *Vaccine Design: The Subunit and Adjuvant Approach* (eds. Powell & Newman) Plenum Press 1995 (ISBN 0-306-44867-X).
[25] *Vaccine Adjuvants: Preparation Methods and Research Protocols* (Volume 42 of *Methods in Molecular Medicine* series). ISBN: 1-59259-083-7. Ed. O'Hagan.
[26] US-2007/014805.
[27] Stephenson et al. (2008) *NEJM* 359:1631-33.
[28] Galli et al. (2009) *PNAS USA* 106:7962-7.
[29] Clinical trial NCT00895544.
[30] US-2009/0028903.

The invention claimed is:

1. A method for raising an immune response in a subject, comprising steps of (i) administering a priming immunogenic composition to the subject, wherein the priming immunogenic composition elicits a primary immune response against a pathogen and then (ii) administering a boosting immunogenic composition to the subject, wherein the priming composition and the boosting composition are administered more than 5 years apart, and wherein the boosting immunogenic composition elicits, within 21 days of its administration, a protective anamnestic immune response against the pathogen, and wherein the pathogen is an influenza A virus having a H5 hemagglutinin.

2. The method of claim 1, wherein the protective anamnestic immune response comprises a neutralizing antibody response and/or opsonizing antibody response.

3. The method of claim 1, wherein the protective anamnestic immune is elicited within 7 days of administration of the boosting composition.

4. The method of claim 1, wherein the priming composition and/or the boosting composition includes an immunological adjuvant.

5. The method, use or immunogen of claim 4, wherein the adjuvant is an oil-in-water emulsion comprising squalene and at least one surfactant.

\* \* \* \* \*